(12) United States Patent
Landry et al.

(10) Patent No.: US 9,808,290 B2
(45) Date of Patent: Nov. 7, 2017

(54) TRANSCUTANEOUS JOINT UNLOADING DEVICE

(75) Inventors: Michael E. Landry, Austin, TX (US); Anton G. Clifford, Mountain View, CA (US); Joshua Makower, Los Altos, CA (US)

(73) Assignee: MOXIMED, INC., Hayward, CA (US)

( * ) Notice: Subject to any disclaimer, the term of this patent is extended or adjusted under 35 U.S.C. 154(b) by 35 days.

(21) Appl. No.: 13/495,440

(22) Filed: Jun. 13, 2012

(65) Prior Publication Data

US 2013/0013067 A1 Jan. 10, 2013

Related U.S. Application Data

(60) Provisional application No. 61/504,886, filed on Jul. 6, 2011.

(51) Int. Cl.
| | |
|---|---|
| *A61B 17/68* | (2006.01) |
| *A61B 17/56* | (2006.01) |
| *A61B 17/64* | (2006.01) |
| *A61B 17/80* | (2006.01) |
| *A61B 17/86* | (2006.01) |

(52) U.S. Cl.
CPC .......... *A61B 17/683* (2013.01); *A61B 17/56* (2013.01); *A61B 17/6425* (2013.01); *A61B 17/80* (2013.01); *A61B 17/86* (2013.01); *A61B 2017/564* (2013.01); *A61B 2017/567* (2013.01)

(58) Field of Classification Search
CPC .. A61F 5/0106; A61F 2/38; A61F 5/01; A61F 5/0102; A61F 5/0123; A61F 5/0132; A61F 2005/0132; A61F 2005/0134; A61F 2005/0137; A61F 2005/0144; A61F 2005/0141; A61F 2005/0146; A61B 17/56; A61B 17/86; A61B 17/683; A61B 17/6425; A61B 17/80; A61B 2017/564; A61B 2017/567
USPC ......... 623/13.11, 13.12, 16.11, 17.13, 18.11, 623/20.14, 20.15, 20.19, 20.2, 20.21, 623/20.24, 21.11, 23.39, 23.41, 32, 39, 42
See application file for complete search history.

(56) References Cited

U.S. PATENT DOCUMENTS

| | | | | |
|---|---|---|---|---|
| 5,103,811 A | * | 4/1992 | Crupi, Jr. ................ | A61F 5/024 602/16 |
| 6,162,223 A | * | 12/2000 | Orsak et al. .................... | 606/59 |
| 6,342,076 B1 | | 1/2002 | Lundborg | |
| 2005/0288670 A1 | | 12/2005 | Panjabi et al. | |
| 2006/0229603 A1 | * | 10/2006 | Olsen .............................. | 606/54 |

(Continued)

OTHER PUBLICATIONS

Supplementary European Search Report for European Patent App. No. 12807819.3 (dated Feb. 9, 2015).

(Continued)

*Primary Examiner* — Christopher D Prone
*Assistant Examiner* — Rokhaya Diop
(74) *Attorney, Agent, or Firm* — Cermak Nakajima & McGowan LLP; Adam J. Cermak

(57) ABSTRACT

Various methods for treating a joint are disclosed herein. According to one method, a joint is surgically treated by performing a surgical repair treatment on tissue within the joint capsule; implanting a load reducing device at the joint and entirely outside of the joint capsule to reduce load transmitted by the treated tissue to allow for the tissue within the joint capsule to heal; and partially unloading the joint during healing of the surgical repair site.

16 Claims, 6 Drawing Sheets

(56) References Cited

U.S. PATENT DOCUMENTS

| | | |
|---|---|---|
| 2007/0161984 A1 | 7/2007 | Cresina et al. |
| 2008/0275555 A1 | 11/2008 | Makower et al. |
| 2008/0275557 A1* | 11/2008 | Makower et al. ......... 623/18.11 |
| 2010/0145336 A1 | 6/2010 | Draper |
| 2010/0145449 A1 | 6/2010 | Makower et al. |
| 2011/0093012 A1 | 4/2011 | Gittings |

OTHER PUBLICATIONS

Office Action from U.S. Appl. No. 14/459,959 (dated May 28, 2015).
Final Office Action for U.S. Appl. No. 14/459,959 (dated Feb. 19, 2016).

* cited by examiner

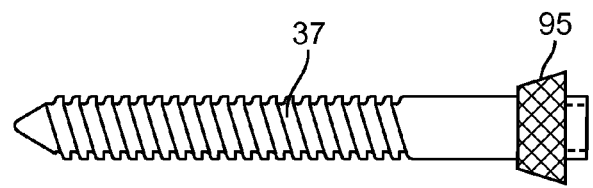
FIG. 8A
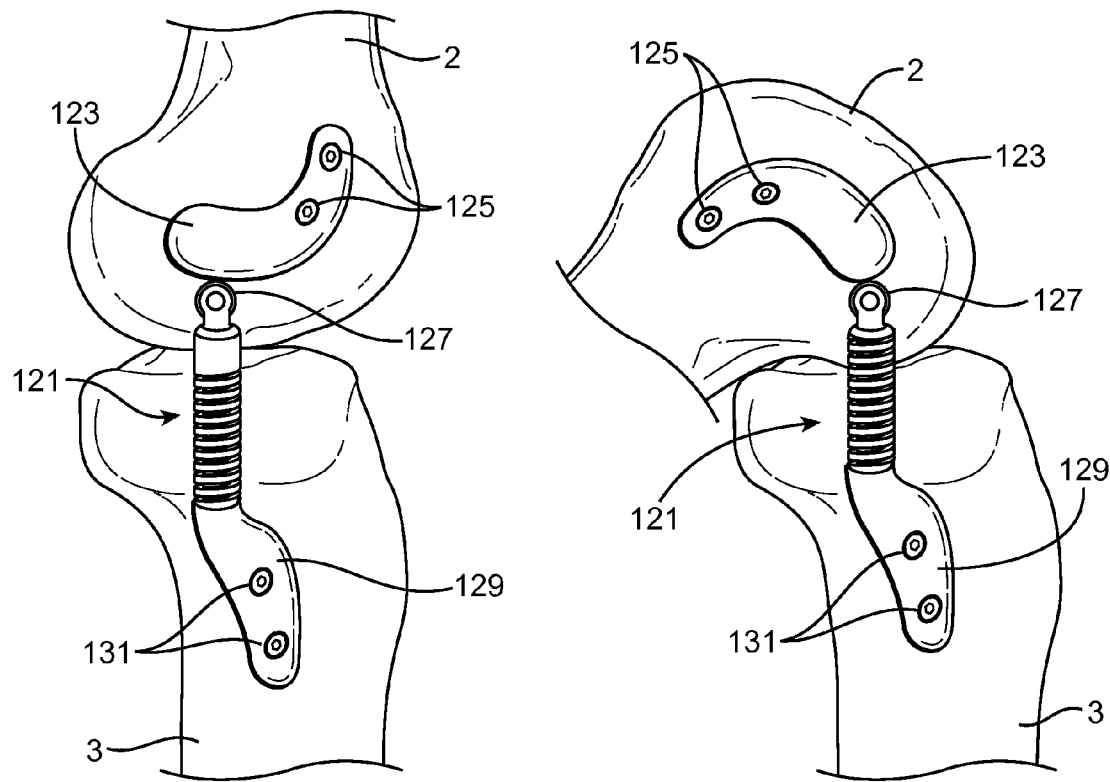
FIG. 9A
FIG. 9B

TRANSCUTANEOUS JOINT UNLOADING DEVICE

CROSS REFERENCES TO RELATED APPLICATIONS

This application claims the benefit of U.S. Application Ser. No. 61/504,886, filed Jul. 6, 2011, the entire disclosure of which is expressly incorporated herein.

BACKGROUND AND SUMMARY

The present invention relates to a joint unloading device and, more particularly, to a transcutaneous joint unloading device.

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced. Arthroplasty as a general term, is an orthopaedic procedure which surgically alters the natural joint in some way. This includes procedures in which the arthritic or dysfunctional joint surface is replaced with something else, procedures which are undertaken to reshape or realigning the joint by osteotomy or some other procedure. As with joint replacement, these other arthroplasty procedures are also characterized by relatively long recovery times and are highly invasive procedures. A previously popular form of arthroplasty was interpositional arthroplasty in which the joint was surgically altered by insertion of some other tissue like skin, muscle or tendon within the articular space to keep inflammatory surfaces apart. Among other types of arthroplasty are resection(al) arthroplasty, resurfacing arthroplasty, excisional arthroplasty, mold arthroplasty, cup arthroplasty, silicone replacement arthroplasty, and osteotomy to affect joint alignment or restore or modify joint congruity. When it is successful, arthroplasty results in new joint surfaces which serve the same function in the joint as did the surfaces that were removed. Any chondrocytes (cells that control the creation and maintenance of articular joint surfaces), however, are either removed as part of the arthroplasty, or left to contend with the resulting joint anatomy. Because of this, none of these currently available therapies are chondro-protective.

Other approaches to treating osteoarthritis involve an analysis of loads which exist at a joint. Both cartilage and bone are living tissues that respond and adapt to the loads they experience. Within a nominal range of loading, bone and cartilage remain healthy and viable. If the load falls below the nominal range for extended periods of time, bone and cartilage can become softer and weaker (atrophy). If the load rises above the nominal level for extended periods of time, bone can become stiffer and stronger (hypertrophy). Finally, if the load rises too high, then abrupt failure of bone, cartilage and other tissues can result. Accordingly, it has been concluded that the treatment of osteoarthritis and other bone and cartilage conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there is a need for devices which facilitate the control of load on a joint undergoing treatment or therapy, to thereby enable use of the joint within a healthy loading zone.

Certain other approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain but have ultimately been unsuccessful due to patient discomfort or the inability of the devices to facilitate and support the natural motion and function of the diseased joint.

One new approach to treating osteoarthritis involves implantation of an extra-articular implantable joint unloading device which is positioned alongside the painful joint and bears some of the load normally borne by the joint. This unloading device reduces pain by cushioning the joint from excessive loading. Since the device is extra-capsular and extra-articular, no bone, ligament, or cartilage is removed and future treatment options, such as joint replacement, are still available if needed. However, for some patients a more temporary solution may be more attractive. Patients and physicians may also be interested in providing an unloading device in which a portion of the device is external for ease of adjustment and removal.

With the foregoing applications in mind, it has been found to be desirable to develop temporary joint unloading structures for mounting to body anatomy with at least a portion of the unloading structure external and removable. Such structures should conform generally to body anatomy and cooperate with body anatomy to achieve desired load reduction, energy absorption, energy storage, and energy transfer. For these implant structures to function optimally, they must not cause an adverse disturbance to joint motion. Therefore, what is needed is an approach which addresses both joint movement and varying loads as well as complements underlying or adjacent anatomy.

Briefly and in general terms, the present disclosure is directed towards treating diseased or mal-aligned body joints, typically affected by osteoarthritis, using a transcutaneous joint unloading device without limiting the range of motion of the patient's articulating joint. The devices of the present invention accomplish one or more of: absorbing energy during normal gait, reducing load on at least a portion of the natural joint, load transferring or bypassing, energy cushioning, and load sharing, unloading or load redistribution. In addition, both energy dampening and shock absorption are considered in effecting such load manipulations. Further, the particular anatomy of a patient is considered in the contemplated approaches in that loads on desired portions of anatomy are manipulated without overloading healthy surfaces. In a preferred aspect, the present invention adds an energy absorber to the joint to reduce energy transferred through the natural joint. One aspect includes a system for manipulating or absorbing energy transferred by members defining a joint.

According to an aspect of the present invention, a transcutaneous unloading device for a joint comprises a load absorber having a first and a second mating portion, a load absorbing portion disposed between the first and the second mating portions, and the load absorbing portion comprising a single load absorbing pivot, a first percutaneous anchor having a first anchor portion configured to be affixed to a first member of the joint, and a first anchor mating portion for mating with the first mating portion, and a second percutaneous anchor having a second anchor portion configured to be affixed to a second member of the joint, and a second anchor mating portion for mating with the second mating portion, wherein the first and second mating portions and the first and second anchors are configured so that the load absorbing portion is disposed externally of a user's skin and so that the load absorbing pivot is pivotable at least about an axis substantially aligned with an axis of rotation of the first and second members of the joint.

According to another aspect of the present invention, a method of treating a joint comprises attaching a first anchor portion of a first percutaneous anchor to a first member of the joint, attaching a second anchor portion of a second percutaneous anchor to a second member of the joint, and attaching a load absorber to the first and second anchors so that a load absorbing portion of the load absorber is disposed externally of a user's skin by attaching a first and a second mating portion of the load absorber to first and second anchor mating portions of the first and second anchors, the load absorbing portion being disposed between the first and the second mating portions, the load absorbing portion comprising a single load absorbing pivot, the load absorber being attached so that the load absorbing pivot is pivotable at least about an axis substantially aligned with an axis of rotation of the first and second members of the joint.

According to another aspect of the present invention, a transcutaneous unloading device for a joint comprises a load absorber having a first and a second mating portion and a load absorbing portion disposed between the first and the second mating portions, a first percutaneous anchor having, at a first end thereof, a first anchor portion configured to be affixed to a first member of the joint, and, at a second end thereof, a first anchor mating portion for mating with the first mating portion, and a second percutaneous anchor having, at a first end thereof, a second anchor portion configured to be affixed to a second member of the joint, and, at a second end thereof, a second anchor mating portion for mating with the second mating portion, wherein the first and second mating portions and the first and second anchors are configured so that the load absorbing portion is disposed externally of a user's skin, and first ends of the first and second anchors are disposed on opposite ends of the first and second anchors from the second ends of the first and second anchors and are configured to be disposed subcutaneously.

According to another aspect of the present invention, a method of treating a joint, comprises attaching a first anchor portion at a first end of a first percutaneous anchor to a first member of the joint, attaching a second anchor portion at a first end of a second percutaneous anchor to a second member of the joint, and attaching a load absorber to the first and second anchors so that a load absorbing portion of the load absorber is disposed externally of a user's skin by attaching a first and a second mating portion of the load absorber to first and second anchor mating portions of the first and second anchors at second ends of the first and second anchors opposite the first ends of the first and second anchors, the load absorbing portion being disposed between the first and the second mating portions, and the first ends of the first and second anchors being disposed subcutaneously.

According to another aspect of the present invention, a transcutaneous unloading device for a joint comprises a single load absorber having a first and a second mating portion and a load absorbing portion disposed between the first and the second mating portions, a first percutaneous anchor having a first anchor portion configured to be affixed to a first member of the joint, and a first anchor mating portion for mating with the first mating portion, and a second percutaneous anchor having a second anchor portion configured to be affixed to a second member of the joint, and a second anchor mating portion for mating with the second mating portion, wherein the first and second mating portions and the first and second anchors are configured so that the load absorbing portion is disposed externally of a user's skin only on one side of the joint.

According to another aspect of the present invention, a method of treating a joint comprises attaching a first anchor portion of a first percutaneous anchor to a first member of the joint, attaching a second anchor portion of a second percutaneous anchor to a second member of the joint, and attaching a single load absorber to the first and second anchors so that a load absorbing portion of the load absorber is disposed externally of a user's skin only on one side of the joint by attaching a first and a second mating portion of the load absorber to first and second anchor mating portions of the first and second anchors, the load absorbing portion disposed between the first and the second mating portions.

According to another aspect of the present invention, a transcutaneous unloading device for a joint comprises a load absorber having a first and a second mating portion and a load absorbing portion disposed between the first and the second mating portions, a first percutaneous anchor having a first anchor portion configured to be affixed to a first member of the joint, and a first anchor mating portion for mating with the first mating portion, and a second percutaneous anchor having a second anchor portion configured to be affixed to a second member of the joint, and a second anchor mating portion for mating with the second mating portion, wherein the first and second mating portions and the first and second anchors are configured so that the load absorbing portion is disposed externally of a user's skin, and wherein the first and the second mating portions and the first and second anchor mating portions comprise quick-disconnect couplings.

According to another aspect of the present invention, a method of treating a joint comprises attaching a first anchor portion of a first percutaneous anchor to a first member of the joint, attaching a second anchor portion of a second percutaneous anchor to a second member of the joint, and attaching a load absorber to the first and second anchors so that a load absorbing portion of the load absorber is disposed externally of a user's skin by attaching a first and a second mating portion of the load absorber to first and second anchor mating portions of the first and second anchors, the load absorbing portion disposed between the first and the second mating portions, wherein the first and the second mating portions and the first and second anchor mating portions comprise quick-disconnect couplings.

According to another aspect of the present invention, a transcutaneous unloading device for a joint comprises a load absorber having a first and a second mating portion and a load absorbing portion disposed between the first and the second mating portions, a first percutaneous anchor having a first anchor portion configured to be affixed to a first member of the joint by at least one bone screw, and a first anchor mating portion for mating with the first mating portion, and a second percutaneous anchor having a second anchor portion configured to be affixed to a second member of the joint by one bone screw, and a second anchor mating portion for mating with the second mating portion, wherein the first and second mating portions and the first and second anchors are configured so that the load absorbing portion is disposed externally of a user's skin.

According to another aspect of the present invention, a method of treating a joint comprises attaching a first anchor portion of a first percutaneous anchor to a first member of the joint by at least one bone screw, attaching a second anchor portion of a second percutaneous anchor to a second member of the joint by one bone screw, and attaching a load absorber to the first and second anchors so that a load absorbing portion of the load absorber is disposed externally of a user's skin by attaching a first and a second mating portion of the load absorber to first and second anchor mating portions of the first and second anchors, the load absorbing portion disposed between the first and the second mating portions.

Other features of the unloading device and device will become apparent from the following detailed description, taken in conjunction with the accompanying drawings, which illustrate, by way of example, the principles of the embodiments.

BRIEF DESCRIPTION OF THE DRAWINGS

The features and advantages of the present invention are well understood by reading the following detailed description in conjunction with the drawings in which like numerals indicate similar elements and in which:

FIG. 8A is a side view of one example of an anchor;

FIG. 9A is a side view of another embodiment of the joint unloading device; and

FIG. 9B is a side view of the joint unloading device of FIG. 9A is a flexed condition.

DETAILED DESCRIPTION

Figure 1:
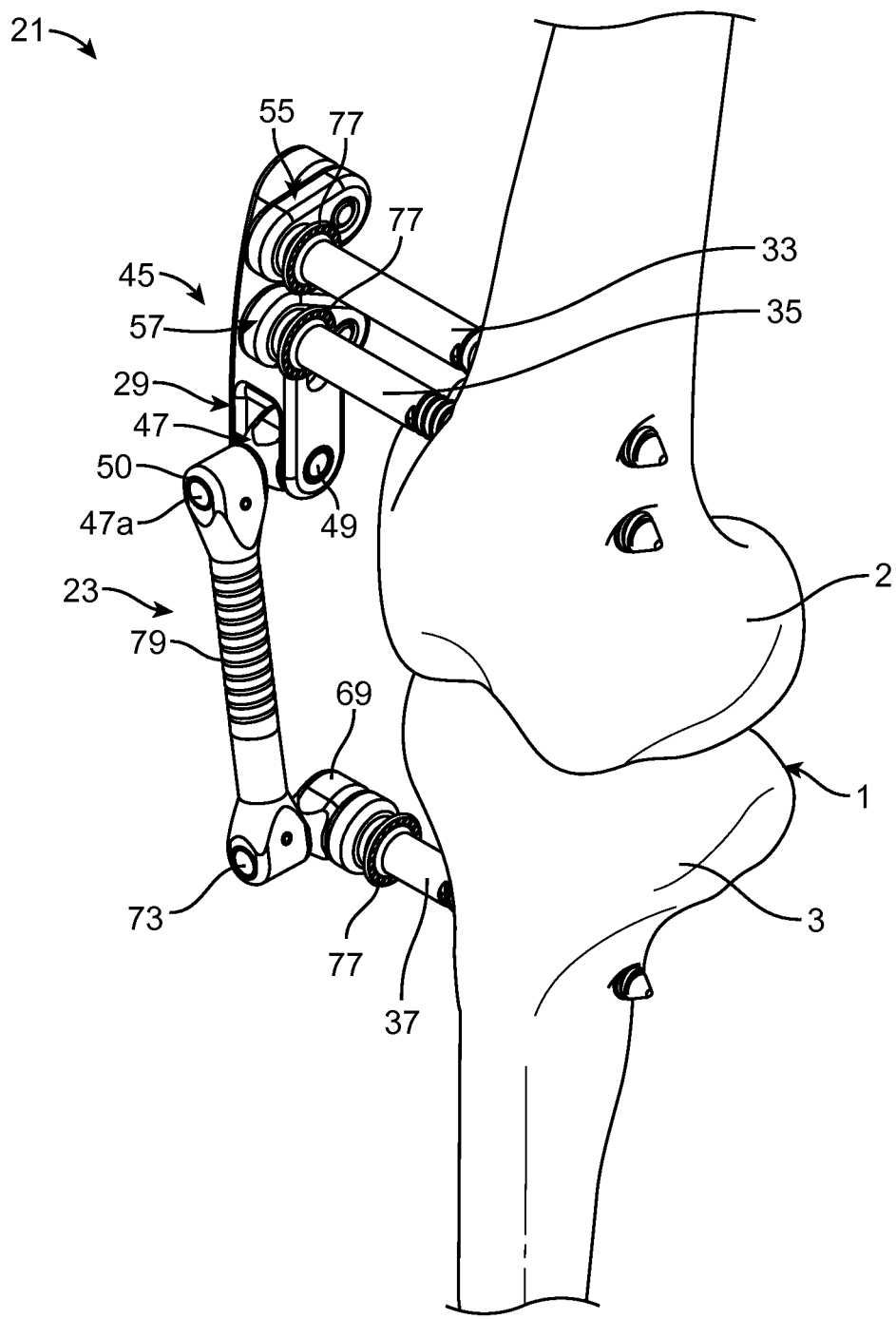
FIG. 1 is a perspective view of a joint unloading device according to an aspect of the present invention.

Referring now to the drawings, which are provided by way of example and not limitation, the disclosed embodiments are directed to apparatus and methods for treating the knee joint. However, these embodiments may also be used in treating other body joints, and to alleviate pain associated with the function of diseased or misaligned members forming a body joint while preserving range of motion of the joint. The embodiments described below relate to apparatuses and methods for reducing the amount of load carried by the natural joint anatomy.

Certain of the embodiments include joint unloading devices designed to minimize the loading of the anatomy of the body, such as that found at a body joint. It has been postulated that to minimize pain, unloading or load absorption of 1-40% of the forces on the joint, in varying degrees, may be necessary. Variable unloading or energy absorption in the range of 5-20% can be a target for certain applications.

It has also been found that a medial compartment of a knee of an average person with osteoarthritis can benefit from an absorber set for compression between 1 mm and 10 mm, and preferably 3-6 mm with a spring or absorber element that accommodates a range from 20-60 pounds, preferably 20-40 pounds. In a preferred embodiment, the absorber is set for about 4 mm of such compression and a pre-determined load of about 30-40 pounds.

When a joint unloading device is attached to a joint as described below, less force is transferred through the bones and cartilage of the joint, and a degree of the force between bones of the joint is absorbed by the unloading device. In one embodiment, the joint unloading device can be initially configured to eliminate, variably reduce or manipulate loads at a first desired amount, and to be later adjusted or altered as patient needs are better determined or change to a second desired amount. The unloading device can be adjusted periodically or can be automatically adjusting based on feedback provided by the device.

In applications to the knee joint, the unloading device can be positioned only on the medial side of the knee and designed to absorb medial compartment loads in a manner that completely preserves the articulating joint and capsular structures. In other application, the unloading device can be positioned and designed for unloading the lateral compartment of the knee joint or both the medial and lateral compartments of the knee.

One embodiment of the present invention is a transcutaneous knee unloading device comprised of an external kinematic load absorber including at least one spring attached to transcutaneous bone anchors. Although the illustrated embodiment is designed for use with a knee joint, the device can be applied to the ankle, hip, and other joints.

A transcutaneous knee unloading device 21 according to an aspect of the invention for a knee joint 1 is seen in FIGS. 1-8. The knee joint 1 comprises a first member 2, which may be a femur, and a second member 3, which may be a tibia. The device 21 shown in FIGS. 1-8 is shown as having an external component on a medial side of a left knee joint 1, but it will be appreciated that an external component of the device may be disposed on the lateral side of the joint, or on a right joint. As shown in phantom in FIG. 3, an external component of the device 21 may be disposed bilaterally, i.e., on both the lateral and medial sides of the joint 1.

The device 21 comprises a load absorber 23 that is ordinarily entirely or at least substantially outside of the user's skin. The load absorber 23 has a central load absorbing portion disposed between first and the second mating portions. The device 21 further comprises first and second transcutaneous anchors 33 and 35 in the form of bone screws each having a first threaded end configured to be affixed to the first member 2 of the knee joint 1, and a mating end for mating with the first mating end of the load absorber 23. The device also comprises a third transcutaneous anchor 37 having a threaded end configured to be affixed to the second member 3 of the knee joint 1, and a mating end for mating with the second mating end of the load absorber 23.

Figure 3:
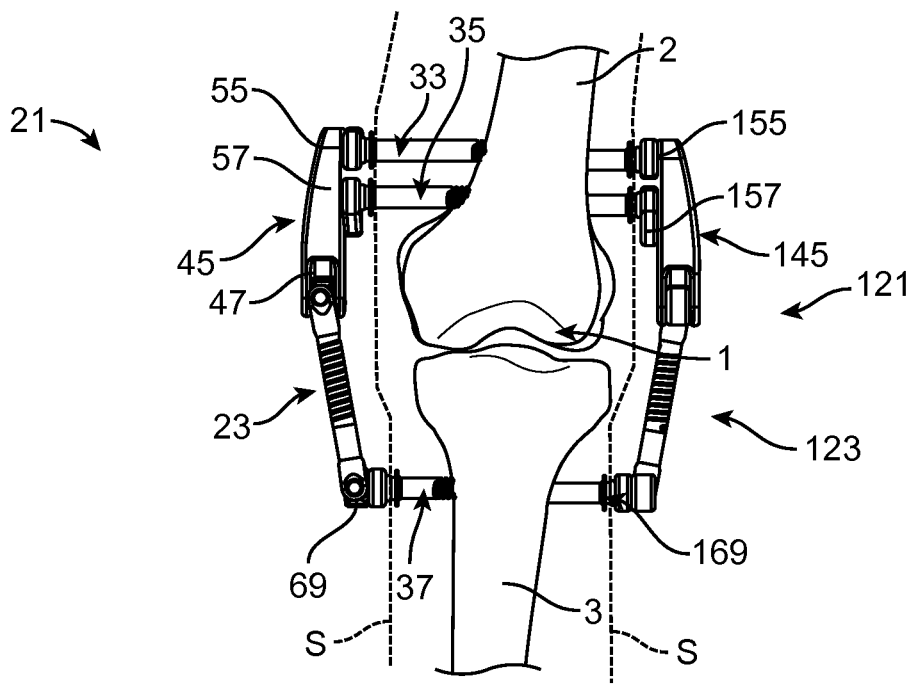
FIG. 3 is a front view of the joint unloading device of FIG. 1 showing a bilateral version.
Figure 4:
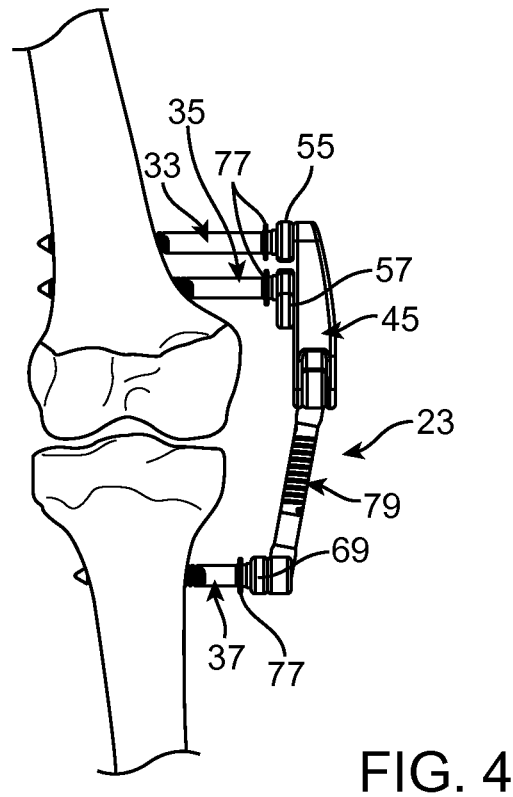
FIG. 4 is a rear view of the joint unloading device of FIG. 1 showing a unilateral version.
Figure 5:
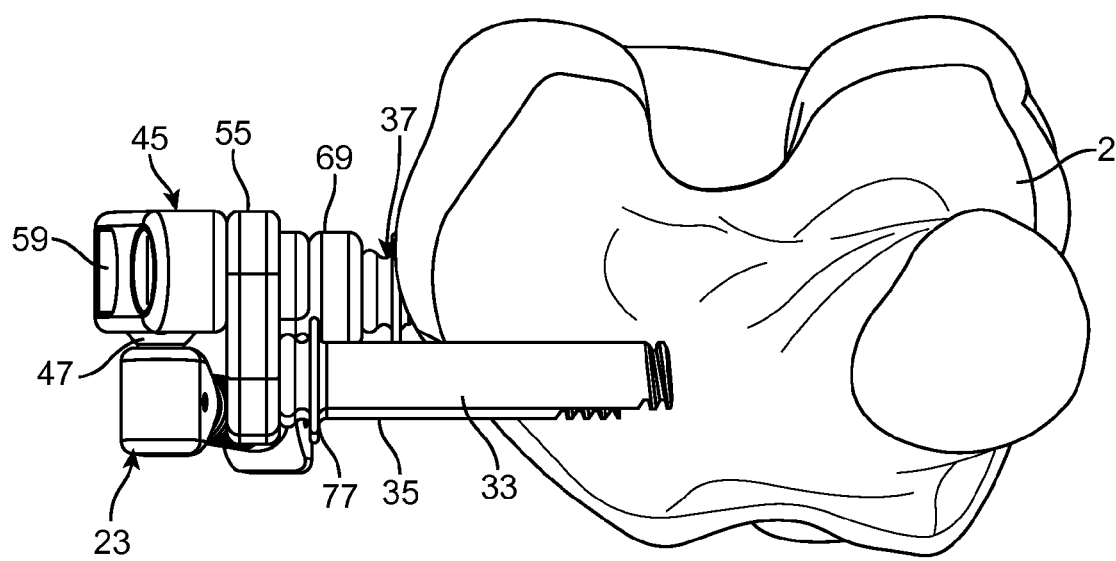
FIG. 5 is a top view of the joint unloading device of FIG. 1.
Figure 6:
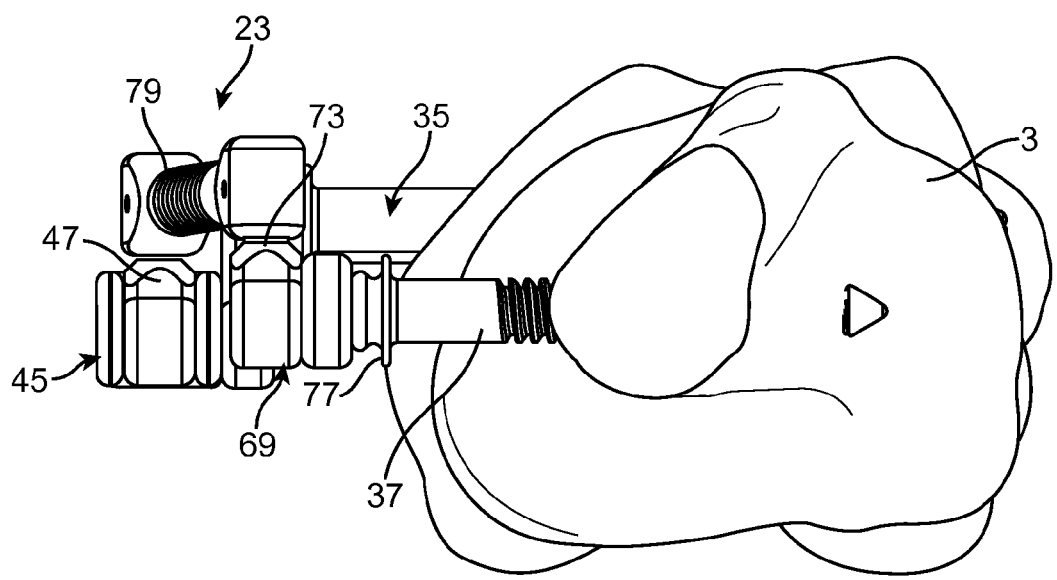
FIG. 6 is a bottom view of the joint unloading device of FIG. 1.

The load absorber 23 and the first, second and third anchors 33, 35 and 37 are configured so that at least a portion of the load absorber is disposed externally of a user's skin S (shown by dotted lines in FIG. 3). Thus, the load absorber 23 can be attached and detached from the first, second and third anchors 33, 35 and 37 which are secured in the bone.

The attachment and detachment of the load absorber 23 can be accomplished by the patient or physician and depending on the type of attachment can be done with or without tools. The patient may remove the absorber 23 during times of inactivity, such as when sleeping, bathing or sitting at a desk and may attach the absorber during all waking hours or only during active time periods.

As the bone anchors 33, 35 and 37 are designed to traverse the skin of the patient, certain precautions can be implemented to prevent the transmission of microorganisms at the skin penetration site. In one embodiment, the anchors 33, 35 and 37 can have a coating to reduce the possibility of infections, for example, titanium anchors can be provided with a silver anti-infective coating. Other known coatings and precautionary methods can also be used. Other precautions for prevention of infection can include specific cleaning and maintenance steps to be performed by the patient. For example, adhesive coverings may be provided for the exposed ends of the bone anchors when they are not in use.

In another embodiment, a porous tissue cuff can be secured around the bone anchors 33, 35, 37 to prevent infection at the tissue penetration site. A tissue cuff 95 as shown in FIG. 8A is secured to the bone anchor 37 and promotes skin ingrowth into the cuff to provide a barrier to microorganisms. Attachment of the skin to the tissue cuff 95 can be initially preformed by suturing, followed by tissue growth. The secure attachment between the cuff 95 and the skin eliminates pathways for microorganisms to enter the body. Examples of materials for use in the tissue cuff 95 include ePTFE, PTFE and other materials used for synthetic vascular grafts. The material of the tissue cuff 95 should be flexible and avoid irritation of adjacent tissue.

The bone anchors can also include flanges or other anchoring structures which allow suturing to the skin. The flanges 77 shown on each of the anchors are arranged to lie just below the surface of the patient's skin. The flanges 77 can be provided with small openings to accommodate sutures for securing the skin around the anchors. Alternatively, other known skin securing systems can be used to secure the skin to the anchors.

The bone anchors 33, 35 and 37 as shown in the present application are designed to have a top surface which do not protrude from the surface of the skin to prevent any discomfort of protruding parts when the device is removed. Alternately, other anchor structures can be used which protrude somewhat from the bone, however, preferably the bone anchors do not protrude more than about 5 mm from the skin surface.

The unloading device 21 comprises an energy absorber 23 and an arm 45 that are pivotably attached to each other via one or more pivot links. A first pivot link 47, shown in FIG. 1, is mounted in a recess 29 in the lower end of the arm 45 and also includes a pivot post 47a that extends in an anterior direction and is secured in and pivotable relative to an opening 50 in the energy absorber 23. The first pivot link 47 permits pivoting of the arm 45 relative to the energy absorber 23 in two dimensions including about a first axis normal to the user's coronal plane and a second axis perpendicular to the first axis direction.

As shown in FIG. 1 first pivot link 47 includes the pivot post 47a which permits angulation of the external surfaces of the arm 45 and absorbing portion 43 with respect to one another. Rotation about the pivot post 47a accommodates varus/valgus angulation of the joint. The first pivot link 47 also provides relative pivoting of the absorber 23 and the arm 45 at least about a pivot post 49 which is arranged along an axis substantially normal to the user's sagittal plane and extends through the pivot link 47. The pivot post 49 allows flexion/extension motion of the joint 1 and provides the largest range of motion of the unloading device 21. The pivot post 49 is ordinarily arranged to be located substantially parallel with an axis of rotation of the first and second members 2 and 3 of the joint 1. Positioning the pivot post 49 directly on the axis of rotation of the joint provides for unloading force throughout rotation of the joint and throughout the gait of the patient. However, the device 21 facilitates positioning the pivot point 49 in a variety of locations relative to the axis of rotation of the knee joint 1 to obtain various unloading responses. A pivot point 49 just slightly anterior and superior of the axis of rotation of the joint provides an unloading device which unloads the joint in full extension and provides no unloading when the knee is beyond some predetermined amount of flexion. Other locations of the pivot point 49 can be used to achieve other unloading profiles during the motion of the joint.

It is presently believed that the first pivot link 47 should be arranged to permit at least 20 degrees or more of hyperextension of the knee joint 1 and at least 140 degrees or more of flexion, it being further believed that 30 degrees of hyperextension and 150-160 degrees of flexion will be sufficient for the vast majority of users and still allow for significant surgical variation. The first pivot link 47 also allows for varus/valgus rotation of the knee joint of at least 10 degrees and preferably at least 30 degrees.

The first and second anchors or bone screws 33 and 35 are connected to the arm 45 by upper and lower links 55 and 57. The lower link 57 is rotatably attached at a first end thereof to the lower screw 35 and at a second end is adjustably attached to the arm 45. The upper link 55 is rotatably attached at a first end thereof the upper screw 33 and at a second end is rotatably attached to the arm 45. The first ends of the upper and lower links 55 and 57 are ordinarily attached to the upper and lower screws 33 and 35 in a manner such the links are substantially unable to transmit moment to the upper and lower screws, such as that the links are attached in a manner so that they are freely rotatable relative to the screws. The links are also preferably detachable from the bone screws 33 and 35 to allow the unloading device to be removed from the bone anchors. One such connection will be described in further detail below with reference to FIG. 8.

Figure 2:
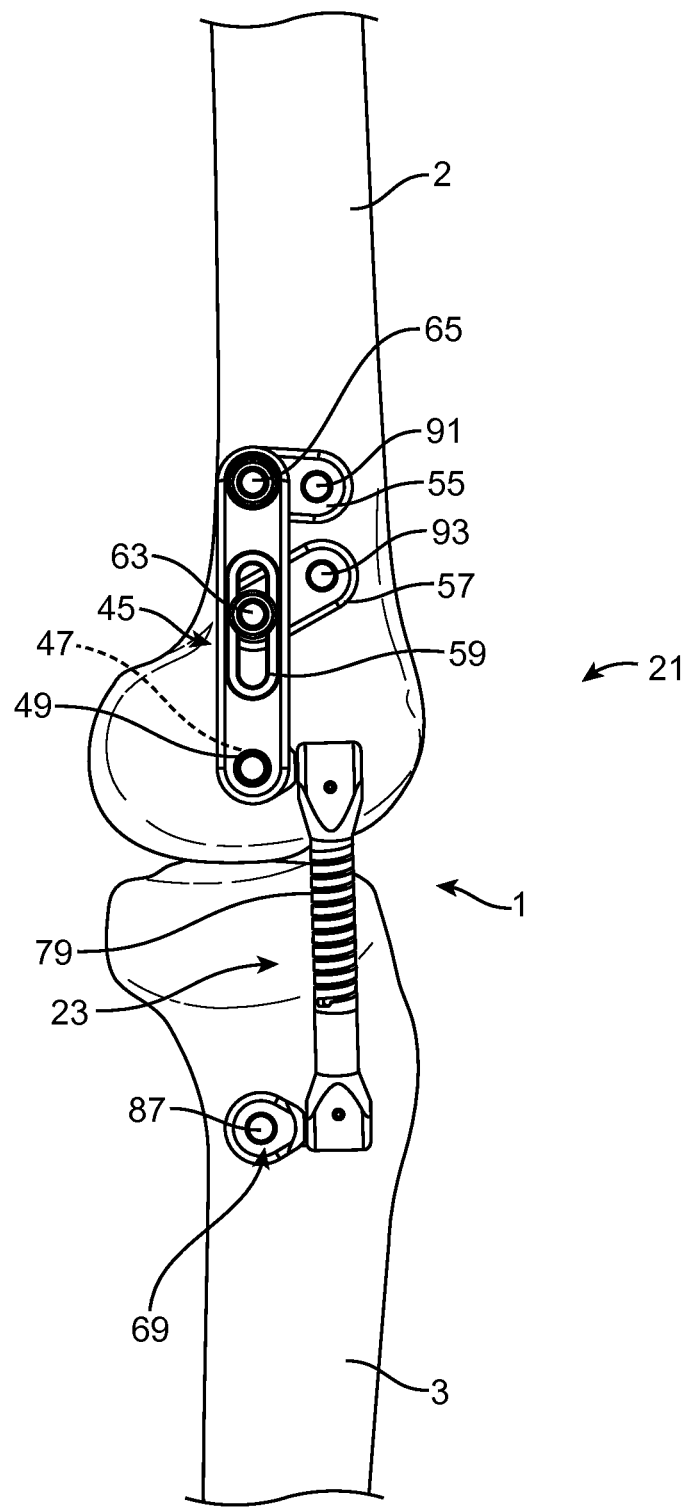
FIG. 2 is a side view of the joint unloading device of FIG. 1.

The links 55 and 57, shown most clearly in FIG. 2, may be the same length but, ordinarily, are of different lengths an allow adjustment of unloading device to a particular patient. Ordinarily, it is desirable for a longitudinal axes of the arm 45 and the femur 2 to be parallel, as shown in FIG. 2, and the device is adjustable to achieve this arrangement as will be described below.

The lower link 57 is adjustable and lockable relative to the arm 45 at one of a plurality of locking points. As shown in FIG. 2, the arm 45 comprises a longitudinal slot 59 and the lower link 57 comprises fastener 63 at the second end of the lower link. The fastener extends through the slot 57 and threads into an internally threaded hole in the lower link 57 to secure the link 57 to the arm 45 at any locking position along the length of the slot. Ordinarily, the fastening arrangement between the arm 45 and the lower link 57 will be one that will prevents relative angular between the longitudinal axes of the arm and the lower link once the fastener 63 has been tightened. Changing the locking point of the lower link 57 relative to the arm 45 changes a location of the absorber pivot point 49 relative to the knee joint 1 and can change the overall function of the device.

While locking the lower link 57 to the arm 45 in this fashion can serve to also set the relative position of the upper link 55 relative to the arm, ordinarily, the upper link is also locked to the arm, such as by a threaded fastener 65 extending through the upper end of the arm 45 and into a threaded hole in the upper link 55. When at least the lower link 57 is locked relative to the arm 45, the upper and lower links 55 and 57 form a plurality of pairs of upper and lower link angles relative to the arm. Changing the upper and lower link angles ordinarily changes a location of the pivot point 49 relative to the first and second members 2 and 3 of the knee joint 1. Selection of the length of the lower link 57 relative to the length of the upper link 55 can impact the variety of angles that the arm 45 can form with the first member 2 of the knee joint 1 and the position of the pivot point 49. Longitudinal axes of the upper and lower links 55 and 57 ordinarily extend substantially perpendicularly to longitudinal axes of the upper and lower screws 33 and 35 when the screws are parallel.

The energy absorber, also called a load absorber 23 is ordinarily pivotably attached to the third anchor 37, by a second pivot link 69 that permits pivoting of the absorber relative to the second anchor in two dimensions. Similar to the first pivot link 47, the second pivot link 69 has a pivot post 73 which extends in an anterior direction from the third anchor 37 and is received in an opening in the lower end of the energy absorber 23. The pivot post 73 pivotably connects the second pivot link 69 to the energy absorber allowing varus/valgus rotation of the joint.

Ordinarily, the second pivot link 69 is removably attached to the third bone anchor screw 37 in a manner that at least substantially precludes transmission of moment to the screw 37, i.e., the second pivot link is ordinarily freely rotatable relative to the anchor screw. It is desirable for the second pivot link 69 to be easily attached to and detached from the anchor screw 37, such as by providing suitable quick-release fittings as discussed below with reference to FIG. 8. The second pivot link 69 can be provided in different sizes to facilitate offsetting the absorber 23 a desired distance from a user's skin.

The bone screws 33, 35 and 37 are ordinarily bicortical screws which pass through the cortical (harder exterior bone) on two opposite sides of the bone to achieve secure and lasting fixation. Although the screws are shown extending out of the opposite side of the bone in FIG. 1, they do not need to pass out of the bone. In the case of the bilateral embodiment of FIG. 3, the screws 33, 35 and 37 pass through the bones and are provided with a fitting to allow securing of the absorber on both sides of the joint with the same bone screws.

The load absorber 23 ordinarily comprises a spring 79 and a telescoping piston and arbor assembly. Alternatively, the spring 79 can serve as the arbor with a piston translating in the interior bore of the spring to accommodate the variable distance between the bones of the joint during rotation. U.S. Patent Application Publication Nos. US20080275565 and US2008/0275555 and U.S. patent application Ser. No. 12/843,381 are incorporated herein by reference and disclose embodiments of spring, piston and arbor assemblies that are suitable for use in connection with the present invention. The load absorber 23 is arranged so that as a user applies load to the knee joint 1, such as by standing, walking or running, the spring 79 will tend to absorb some or all of the force and thereby reduce load on the knee joint.

Figure 7:
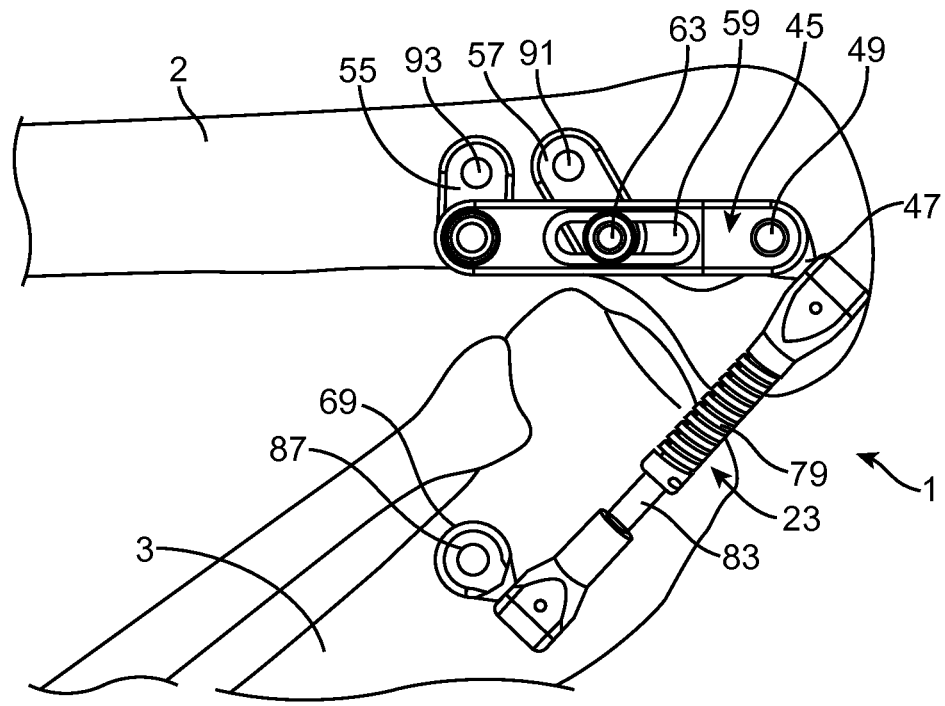
FIG. 7 is a side view of the joint unloading device of FIG. 1 in a flexed condition.

As seen in FIG. 7, when the knee joint is bent, a piston 83 and arbor (beneath the spring) telescope to allow the absorber 23 to extend to accommodate an increasing distance between the first pivot link 47 and the second pivot link 69. Thus, the absorber spring 79 acts in compression to apply a force when the knee joint is in extension and the spring applies no force to the bones in tension when the joint is positioned in flexion as shown in FIG. 7.

The absorber 23 can be provided with quick connection mechanisms (not shown) at both ends for quick attachment to and removal from corresponding connection mechanisms in the upper and lower pivot links 47 and 69 to facilitate changing the absorber 23 for a particular user. For example, absorbers may be provided in different lengths and different spring forces depending on the patient anatomy.

In the bilateral embodiment, as seen in FIG. 3, the unloading device 21 is positioned on the medial side of the knee joint 1 while a second unloading device 121 is positioned on the lateral side of the joint. The bone screw anchors 33, 35 and 37 extend through the bone and are attached to the corresponding upper and lower links 155 and 157 and pivot link 169. A second absorber 123 and second arm 145 can be formed with the same features as those in the medial side device or can be modified for the lateral side of the joint.

Figure 8:
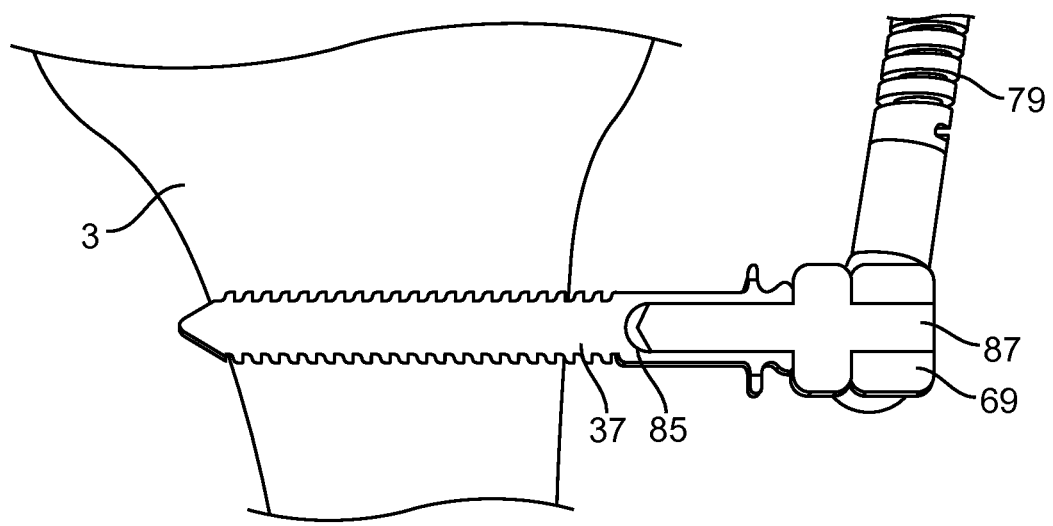
FIG. 8 is a schematic, cross-sectional view of a joint unloading device according to another aspect of the present invention.

FIG. 8 illustrates one example of a quick disconnect fitting for connection to the bone anchors in a removable manner. It is desirable for the upper and lower links 55 and 57 and the pivot link 69 to each be easily attached to and detached from the corresponding bone anchors 33, 35 and 37 either by a physician or a patient. Fittings such as quick-disconnect fittings can be provided to facilitate attachment and removal of the external load absorber 23 from the bone anchors by the user with or without assistance. Examples of quick disconnect fittings include snap lock fittings, taper lock fittings and interference fittings. In one example, as shown in FIG. 8, the quick-disconnect fitting for attaching the pivot link 69 to the bone screw 37 secured in the tibia includes a tapering central bore 85 in the external end of the screw 37 and a corresponding tapered peg 87. The tapered peg 87 also has a mating end for rotatably mating with the pivot link 69. The connections to the first and second bone screws 33 and 35 can also include similar quick connections with tapered pegs 91 and 93. In the event that a physician prefers for the unloading device to be removed only in the doctor's office, more secure fasteners including screws or locking screws can be used.

FIGS. 9A and 9B illustrate an alternative embodiment of an unloading device 121 in which an external cam base 123 is secured to the femur 2 by one or more transcutaneous anchors 125. The cam base 123 cooperates with a follower 127 provided on a follower base 129 which is also positioned external of the knee and secured to the tibia 3 by transcutaneous anchors 131. The follower 127 is shown in the form of a small roller, however, other moving and non-moving followers may also be used. The follower 127 is mounted on the end of an absorber which operates in a manner similar to the absorbers described above to absorb a portion of the forces normally transmitted by the natural knee joint. The cam and follower unloading device 121 provides an external discontinuous unloading device in which one or both bases 123, 129 can be removed to deactivate the device.

A method of treating a knee joint 1 is described with reference to the device 21 shown in FIGS. 1-7. According to the method, first and second transcutaneous anchors 33 and 35 is attached to a first member 2 of the knee joint 1, such as by screwing upper and lower screws 33 and 35 into holes that have been drilled in a femur. A third transcutaneous anchor 37 is attached to a second member 3 of the knee joint 1, such as by screwing into a hole drilled in a tibia. Although two anchors are illustrated on the femur and one on the tibia, other numbers and types of anchors can also be used. The positions of the anchors may be determined by one or more templates or by using the absorber 23 and arm 45 as a guide to determine the proper positioning for the anchors.

A load absorber 23 is attached to the anchors 33, 35 and 37 so that the load absorbing portion is disposed externally of a user's skin. The position of the pivot point 49 relative to the axis of rotation of the first and second members 2 and 3 of the knee joint 1 is adjusted by changing an angle of the lower link 57 in the manner described above.

Because the femur has six degrees of freedom relative to the tibia, it is desirable that a load absorbing device have at least four degrees of freedom, and preferably at least six degrees of freedom. The device 21 according to an aspect of the invention has six degrees of freedom as follows. The two pivot links 47 and 69 with each provide two degrees of freedom; about the pivot posts 47a, 49 and 73 and about the peg 87; linear movement of the piston 83 relative to the spring 79 provides one degree of freedom; and rotational movement of the piston 83 relative to the spring and arbor provides one degree of freedom. While the device 21 illustrated in FIGS. 1-8 provides motion with rotational joints, it will be appreciated that other types of joints and bearings, such as three degree of freedom spherical bearings, can be used instead.

The unloading device 21 according to an aspect of the invention can be useful where the bones proximate the knee joint limit the locations in which femoral and tibial anchors can be provided. Even if it is necessary to provide the anchors at a distance from a location at which they would normally be installed, simple external adjustments can ensure that the pivot points of the device will be at desired locations. These adjustments can be accomplished after attachment of the anchors. In this case, the arm 45, links 55 and 57, pivot link 69, and absorber 79 can be selected among elements provided in varying lengths.

The unloading device 21 according to an aspect of the invention can be versatile. The device shown in FIGS. 1-8 is illustrated used on a left medial knee, however, it could also be used on a right medial knee with the same parts rotated about various pivots. A device for use on left or right lateral knees, such as the device 121 of FIG. 3, will be similar to the device 21, however, somewhat different anatomical considerations may require alterations.

The unloading device 21 according to an aspect of the invention can be used as a more temporary version of devices that are normally provided subcutaneously. This can be particularly useful for temporary unloading of the knee joint after another surgical procedure including cartilage repair or regeneration to allow the surgical site to heal under reduced loading conditions. The device may also be useful for users who are hesitant to undergo a procedure to have a fully implantable system. The device can be implanted minimally invasively with only a few load bearing screws inserted into the bone.

The device can be intraoperatively or post-operatively adjusted. For example, the device can be adjusted post-operatively as further or less load manipulation becomes necessary. Moreover, the device can be activated and adjusted to absorb energy to desired degree or can be deactivated so that no energy absorbing occurs, such as just subsequent to implantation during a period of healing. In this way, a natural healing process where tissue and bone at the interventional site grows to help in fixation of the structure can be allowed to progress prior to activating the load manipulating capabilities of the absorber.

The device can be used to provide load manipulation throughout a wide spectrum of joint unloading from complete unloading and even distraction of the joint to lower levels of partial unloading depending on the clinical situation of the patient. Advantageously, the external unloading device allows for changing clinical needs during the healing process or progression of a clinical condition. For patients seeking pain relief from osteoarthritis pain in a joint, it has also been found that a medial compartment of a knee of an average person with osteoarthritis can benefit from an absorber element that unloads the joint in a range from 20-60 pounds, preferably 20-40 pounds. However, this unloading may be adjusted further depending patient specific factors including patient size, pain level and activity level. Adjustments can be made by periodically by a physician to address patient reported pain or can be made by the patient at a physician's instruction during changing daily activity. For pain relief, the unloading is desired through only a portion of the gait cycle including the stance phase of the gait cycle.

The device can also be used for temporarily for complete unloading or distraction to facilitate tissue regeneration in patients recovering from joint surgery or trauma. Although permanent complete unloading would be negative to joint vitality, temporary unloading of 100% of the joint forces or even distraction of the joint can facilitate biological regeneration. When distraction is provided, unloading sufficient to provide a space of about 0.5 to 5.0 mm between the regenerating joint tissues is desired. The 100% unloading or distraction can be maintained for a period of about 2-4 months, preferably about 3 months to allow regeneration without significant negative effects on joint vitality. This complete unloading or distraction should be followed by a reduction in the percent of unloading (joint reloading) over the subsequent 1-3 years. The gradual reloading of the joint can be done in a gradual or stepwise manner with the goal of eliminating the unloading device completely over a period of time. Although complete unloading or distraction are described for promoting tissue regeneration, less than 100% unloading may also be used to promote tissue regeneration. In one example 60% to 100% unloading can be provided to promote tissue regeneration.

In the case of complete or near complete unloading to allow tissue regeneration, unloading may be needed throughout the entire gait cycle or for only a portion of the gait cycle depending on the location of the damaged tissue within the joint. Examples of use of load reducing devices, such as the external unloading devices 21 and 121 of the present invention for load reduction during healing from other surgical procedures is described in U.S. patent application Ser. No. 13/495,428 entitled "Methods and Devices for Partial Joint Offloading During Healing of Joint Tissue," filed on even date herewith and incorporated herein by reference in its entirety.

The device can also incorporate an adjustable energy absorber which can be easily adjusted as the patient's need for unloading of the joint changes. Examples of adjustable energy absorbing devices are described in U.S. Patent Publication No. 2008/0275565 which is incorporated herein by reference in its entirety. Such adjustable absorbers allow the patient of physician to adjust the energy absorbing or absorption device to alter the load manipulating or absorbing function of the device. For example, the physician may adjust the device 21 based on external or internal measurement of the load on the joint or on the absorber. Alternatively or additionally, the patient may adjust the absorber based on a current activity level, leaving the device on a low unloading setting while sitting at a desk and changing to a high unloading setting when exercising.

Moreover, feedback systems can be incorporated into the device to indicate the past performance of the device and help in adjustment for better performance. For example, the device may record data including loading, cycling and time worn.

In each of the disclosed embodiments, various features can be incorporated such as audible and textile feedback sub-systems can be incorporated to both indicate translation of load adjustment structure as well as to exhibit locking and unlocking of subcomponents.

Moreover, the device can include springs machined to provide desirable energy absorbing which varies as the spring is compressed during various degrees of flexion and extension of joint markers to which the unloading device is attached.

The term "spring" is used throughout the description but it is contemplated to include a variety of conventional springs including coil springs, leaf springs and other springs as well as other energy absorbing structures, such as resilient materials can be used to accomplish the functions of the invention. Magnetic, hydraulic, pneumatic or piezoelectric systems can also serve the unloading function of the spring.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While this invention has been illustrated and described in accordance with a preferred embodiment, it is recognized that variations and changes may be made therein without departing from the invention as set forth in the claims.

What is claimed:

1. A transcutaneous unloading device for a joint formed between first and second members, the device comprising:
   a load absorber having a first and a second mating portion, a load absorbing portion disposed between the first and the second mating portions, and the load absorbing portion comprising a load absorbing pivot;
   a first percutaneous anchor having a first anchor portion configured to be affixed to the first member of the joint, a first anchor mating portion configured to mate with the first mating portion, and an axis extending between the first anchor portion and the first anchor mating portion; and
   a second percutaneous anchor having a second anchor portion configured to be affixed to the second member of the joint, a second anchor mating portion configured to mate with the second mating portion, and an axis extending between the second anchor portion and the second anchor mating portion;
   wherein the first and second mating portions and the first and second anchors are configured so that the load absorbing portion is disposed externally of a user's skin when the device is mounted to the first and second joint members and so that the load absorbing pivot is pivotable at least about an axis parallel with an axis of at least one of the first and second percutaneous anchors;
   wherein, between said load absorbing pivot and said second anchor mating portion, the load absorber extends along an axis and is inflexible away from said axis;
   wherein the load absorber comprises
      a rigid arbor extending along said single axis,
      a rigid piston at least partially inside the rigid arbor and movable therein along said single axis, and
      a spring positioned over the piston and over the arbor and movable relative thereto along said single axis.

2. The device of claim 1, wherein the absorber and the arm are pivotable relative to each other about the load absorbing pivot at least about an axis normal to a sagittal plane through the joint when the device is mounted to the first and second joint members.

3. The device of claim 1, wherein the first anchor comprises:
   upper and lower screws; and
   upper and lower links, each link including first and second ends;
   wherein the upper and lower links are adjustably attached at said link first ends to the upper and lower screws, respectively; and
   wherein the upper and lower links are attached at said link second ends to the arm.

4. The device of claim 3, wherein the lower link is lockable relative to the arm at one of a plurality of locking points.

5. The device of claim 4, wherein the arm comprises a slot and the lower link comprises a pin that extends through the slot and a fastener for fastening the pin relative to the slot.

6. The device of claim 4, wherein changing the locking point of the lower link relative to the arm changes a location of the load absorbing portion pivot point relative to the first and second members of the joint.

7. The device of claim 3, wherein longitudinal axes of the upper and lower links extend perpendicularly to longitudinal axes of the upper and lower screws.

8. The device of claim 7, wherein the upper and lower links are:
   adjustably attached to the upper and lower screws and adapted to pivot about the longitudinal axes of the upper and lower screws; and
   locked to the arm so that the upper and lower links form a plurality of pairs of upper and lower link angles relative to the arm.

9. The device of claim 8, wherein changing the upper and lower link angles changes a location of the load absorbing portion pivot point relative to the first and second members of the joint when the device is mounted to the first and second joint members.

10. The device of claim 8, wherein the upper and lower links are adjustably attached to the upper and lower screws so as to not transmit moment to the upper and lower screws.

11. The device of claim 1, wherein the anchor pivot about which the absorber is pivotable relative to the second anchor is configured to permit pivoting at least about an axis normal to a sagittal plane through the joint when the device is mounted to the first and second joint members.

12. The device of claim 11, wherein the absorber and the arm are pivotable relative to each other about the load absorbing pivot at least about an axis normal to said sagittal plane.

13. The device of claim 1, wherein the second anchor comprises an anchor screw and an anchor pin attaching the anchor screw and the absorber.

14. The device of claim 13, wherein the anchor pin is attached to the anchor screw in a manner that precludes transmission of moment to the anchor screw.

15. The device of claim 1, wherein the load absorbing portion comprises a spring.

16. The device of claim 1, wherein the load absorbing portion comprises a variable length arbor.

\* \* \* \* \*